United States Patent [19]  
Manghisi et al.

[11] 3,970,672  
[45] July 20, 1976

[54] 2,2 DISUBSTITUTED-BENZODIOXOLES

[75] Inventors: Elso Manghisi, Monza; Aldo Salimbeni, Milan; Pietro Mennella, Como, all of Italy

[73] Assignee: Istituto Luso Farmaco d'Italia S.r.l., Milan, Italy

[22] Filed: Aug. 6, 1974

[21] Appl. No.: 495,147

[30] Foreign Application Priority Data

Aug. 9, 1973 Italy .................................... 27736/73  
July 4, 1974 Italy .................................... 24811/74

[52] U.S. Cl. ........................ 260/340.5; 260/247.1 S; 260/247.5 H; 260/247.7 Z; 260/293.58; 260/326.8; 424/248; 424/267; 424/274; 424/282
[51] Int. Cl.² ........................................ C07D 317/44
[58] Field of Search ................................ 260/340.5

[56] References Cited  
UNITED STATES PATENTS

| | | | |
|---|---|---|---|
| 2,683,742 | 7/1954 | Cusic | 260/340.5 X |
| 3,787,443 | 1/1974 | Erickson | 424/282 X |
| 3,915,969 | 10/1975 | Manghisi et al. | 260/340.5 X |

FOREIGN PATENTS OR APPLICATIONS

| | | | |
|---|---|---|---|
| 749,380 | 12/1966 | Canada | 260/340.5 |
| 1,220,056 | 1/1971 | United Kingdom | 260/340.5 |

*Primary Examiner*—Ethel G. Love  
*Attorney, Agent, or Firm*—Haseltine, Lake & Waters

[57] ABSTRACT

2,2 Disubstituted-1,3-benzodioxoles having antiflammatory, analgesic, anti-pyretic and anti-tussive action, inhibition or excitation of the central nervous system, local anaesthetic, anti-arrhythmic and hypotensive action, and action inhibiting the aggregation of platelets.

12 Claims, No Drawings

2,2 DISUBSTITUTED-BENZODIOXOLES

This invention provides the 1,3-benzodioxole compounds of the formula:

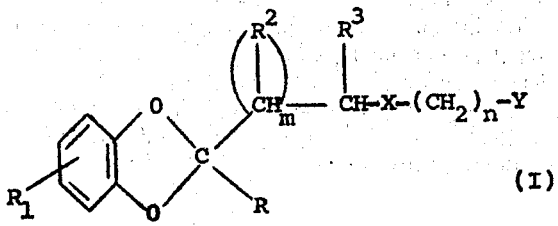

and their optical isomers, stereoisomers, and pharmaceutically acceptable salts, in which R represents hydrogen, lower alkyl, halogeno(lower alkyl), hydroxy (lower alkyl), aryl, arylalkyl, or aryl or arylalkyl substituted by halogen, alkyl, hydroxyl or alkoxyl, or R may be joined to the alkyl chain which is itself bonded to the 2 position of the benzodioxole ring, forming a spirane derivative with 4–7 carbon atoms; $R^1$ represents hydrogen, one or more halogen atoms, lower alkyl, halogeno(lower alkyl), a

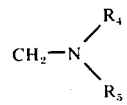

group (where $R_4$ and $R_5$ are as hereinafter defined), hydroxyl, alkoxyl, a sulphonic acid group, sulphamido, N,N-dialkylsulphamido, nitro, amino, substituted amino, or alkylsulphonylamino group, or $R^1$ is a benzene ring condensed on the benzodioxole nucleas, $R^2$ represents hydrogen, alkyl, aryl or hydroxyl; $m$ represents 0, 1 or 2; $R^3$ represents hydrogen, lower alkyl, aryl, hydroxyl or cyano; $n$ represents 0, 1, 2 or 3; X represents O or S; Y represents hydrogen, aryl (substituted or unsubstituted in the aromatic ring with halogen, alkyl, hydroxyl or alkoxyl), a $X-CH_2-CH_2-Y$ group, or a

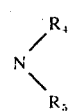

group, wherein

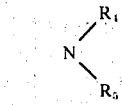

represents a substituted or unsubstituted amino group, in which the substituents are especially hydrogen, lower alkyl, monocyclic carbocyclic aryl, particularly phenyl, or lower monocarbocyclic arylalkyl, particularly phenylalkyl.

The N-monosubstituted amino groups are thus N-alkylamino, for example methylamino, ethylamino or propylamino, N-cycloalkylamino, for example N-cyclohexylamino, N-hydroxyalkylamino, for example N-2-hydroxyethylamino, N-2-hydroxy-2-(3′,5′-dihydroxy)-phenylethylamino, N-arylalkylamino, for example benzylamino, N-dialkylaminoalkylamino, for example N,N-diethylethylenediamino, or N-arylamino, for example N-phenylamino or substituted N-phenylamino.

The N,N-disubstituted amino groups are N,N-dialkylamino, for example N,N-dimethylamino, N-methyl-N-ethylamino, N,N-diethylamino, N,N-di-n-propylamino, or N,N-diisopropylamino, or N-cycloalkyl-N-alkylamino in which the cycloalkyl has 3 to 8 atoms, for example N-cyclopentyl-N-methylamino, or N-cyclohexyl-N-ethylamino, N-lower alkyl-N-phenylalkylamino, for example N-benzyl-N-methylamino, or N-ethyl-N-phenylethylamino, or any other disubstituted amino group, such as N-hydroxyalkyl-N-alkylamino, in which the hydroxyl is separated from the nitrogen by at least two carbon atoms, for example N-ethyl-N-(2-hydroxyethyl)-amino, or N,N-dihydroxyalkylamino, for example N,N-di-(2-hydroxyethyl)-amino.

The

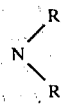

radical may also be a N,N-alkylene imino group in which the alkylene has three to eight carbon atoms, for example 1-pyrrolidino, 1-piperidino, 2-methyl-1-piperidino, 4-hydroxy-4phenyl-1-piperidino, 4-hydroxy-4p-chlorophenyl-1-piperidino, 4-carboxamino-4-phenyl-1-piperidino, 4-benzoylamino-1-piperidino, 4-p-fluorobenzoyl-1piperidino, 1-N,N-(1,6-hexylene)imino, or 1-N,N-(1,7heptylene)imino N,N-oxo-alkylene imino in which the alkylene has preferably four carbon atoms, for example 4-morpholino, N,N-thioalkylene-imino, in which the alkylene has preferably four carbon atoms, for example 4-thio-morpholino, or N,N-azaalkylene-imino in which the alkylene has four to six carbon atoms and in which the "aza" nitrogen can be substituted, for example by a lower alkyl, e.g. methyl, ethyl, or propyl, lower hydroxyalkyl, for example hydroxyethyl, lower alkoxyalkyl, for example methoxyethyl, lower alkoyloxyalkyl, for example acetoxyethyl, lower arylalkyl, for example benzyl, diphenylmethyl, 2-phenylethyl, or 2-3′-indolylethyl, or by a monocarbocyclic aryl, preferably phenyl, substituted or unsubstituted by halogen, alkyl, lower alkoxy or nitro, for example phenyl, 2-tolyl, 2,3-xylyl, 4- chlorophenyl, or 2-methoxyphenyl, or finally by a monocarbocyclic heterocyclic aryl, for example 2-pyridine, 2-furan, or 2-thiophene, and which may be represented by piperazino, 4-methyl-1-piperazino, 4-ethyl-1-piperazino, 4-(2-hydroxyethyl)-1-piperazino, 4-(2-acetoxyethyl)-1-piperazino, 4-benzyl-1-piperazino, 4-[2'-(3'-indolyl)-ethyl]-1-piperazino, 4-phenyl-1-piperazino, 4-p-chlorophenyl-1-piperazino, 4-2'-methoxyphenyl-1-piperazino, 4-2'-pyridyl-1-piperazino and 4-3'-pyridyl-1-piperazino.

Salts can be prepared from the compounds of general formula I containing a basic group, using pharmaceutically acceptable inorganic acids, for example hydrochloric, hydrobromic, nitric, sulphuric, or phosphoric acid, or using organic carboxylic acids, for example acetic, propionic, glycolic, malonic, succinic, maleic, hydroxymaleic, fumaric, malic, tartaric, citric, glucuronic, benzoic, mandelic, salicyclic, 4-aminosalicylic, 2-phenoxybenzoic, pamoic, nicotinic, or isonicotinic acid, or using sulphonic organic acids, for example methanesulphonic, ethanesulphonic, 2-hydroxyethanesulphonic, ethane 1,2-disulphonic, p-toluenesulphonic, or naphthalene-2-sulphonic acid. Mono or poly salts are formed depending on the number of salifiable groups present in the molecule. The invention also comprises the optical isomers and stereo isomers which may be present when one or more of the substituents $R_1$, $R_2$, $R_3$, represent radicals other than a hydrogen atom.

The methods for preparing the aforementioned compounds may be divided into methods for closing the benzodioxole ring to give final or intermediate products, and methods for transforming the functional groups present in the intermediate products (as summarised above) to give those represented in the general formula.

Methods for closing benzodioxoles are known, and are described in application Ser. No. 328,633 applied to the same substrates and others. According to these methods, the benzodioxole ring can be obtained by reacting a pyrocatechol with a ketoalcohol (or ester thereof with an organic or inorganic acid), a ketoester, or a diketone having its carbonyl function in the $\alpha, \beta, \gamma,$ or $\delta$ position with respect to the other group, in a linear, branched or cyclic chain. The carbonyl group may be in the form of a derivative such as an acetal with an aliphatic alcohol, a gem-dichloro or dibromo compound, an enolether or an enamine. The pyrocatechol can be replaced by one of its cyclic derivatives with sulphurous or carbonic acid.

This method thus comprises reacting a pyrocatechol (or reactive derivative thereof) of the formula:

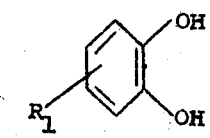

in which $R_1$ is as hereinbefore defined with a ketone compound of the formula:

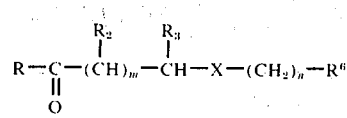

in the presence of a dehydrating agent or an acid catalyst, in which R, $R_2$, $R_3$ and $n$ are as hereinbefore defined, and $R^6$ is hydroxyl, or a derivative thereof reactive with a hydrohalogen acid (hydrobromic or hydrochloric acid) or with an organic oxyacid (such as p-toluenesulphonic acid) or an inorganic oxyacid (such as sulphurous or sulphuric acid) or a Y group where Y has the same meanings as previously given.

Another method consists of reacting pyrocatechol or one of its reactive derivatives as aforesaid with a dibromo derivative of formula:

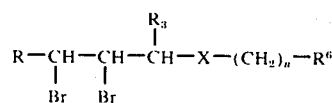

in which R, $n$, $R_3$ and $R_6$ have the meanings given above. Instead of the dibromo derivative, a bromoolefine of formula

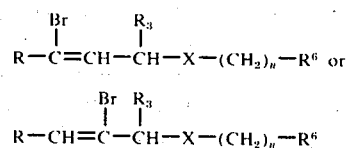

can be used. The benzodioxole may also be obtained by reacting a pyrocatechol with an acetylene derivative of formula:

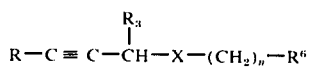

in which the various symbols have the meanings given above.

The intermediates obtained by the above reactions can be transformed into compounds of the general formula I by known organic chemistry methods, i.e. methods heretofore used or described in the chemical literature. In the following description, the various symbols have the above meanings unless otherwise stated. Thus for example, the final products can be obtained by reacting a compound of formula:

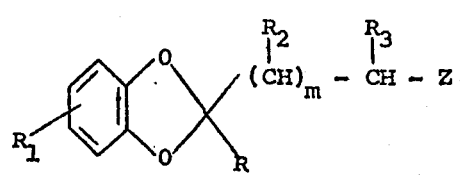

where Z may be a hydroxyl group or one of its derivatives reactive with hydrohalogen acids (hydrobromic or hydrochloric acid) or with organic oxyacids (such as p-toluenesulphonic acid) or inorganic oxyacids (such as sulphurous or sulphuric acid) with a compound of formula:

or by reacting a hydroxy derivative of formula:

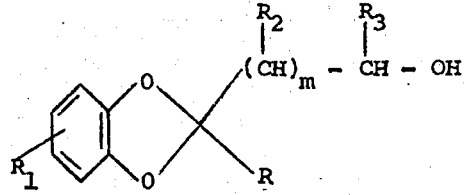

with a halogen derivative of formula:

These reactions may be carried out by suitably reacting the oxyarylated compound, dissolved in a solvent such as benzene or toluene, in the presence of metallic sodium, or sodium hydride, with the halogen derivative at boiling temperature for a period from 1 to a few hours.

The final products can also be obtained by reacting a halogen derivative of formula:

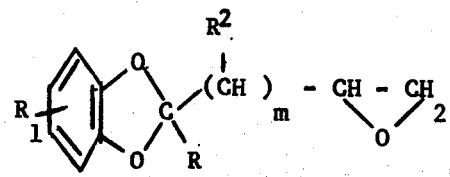

with an amine of formula:

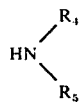

for example by the classical Hofmann method.

When $R^3$ represents a hydroxyl group, the method can be used in which epoxides of formula:

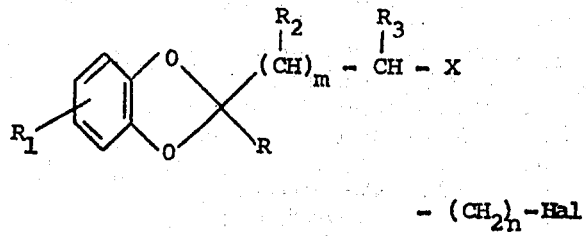

or chlorohydrins of formula:

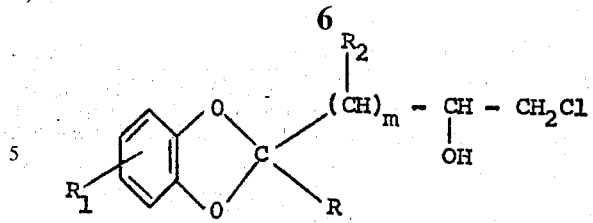

obtained in accordance with the methods described in application Ser. No. 348,096 are reacted with alcohols of formula:

Finally, when $R^1$ represents a halogen, nitro or sulphonic group, it is possible to introduce these substituents directly into the intermediate or final compounds in which $R^1$ represents hydrogen (i.e. by halogenation, nitration or sulphonation in accordance with known methods).

The benzodioxole derivatives of the invention have interesting pharmacological properties, and, according to the substituents present, show anti-inflammatory, analgesic, antipyretic and anti-tussive action, inhibition or excitation of the central nervous system, local anesthetic, antiarrhythmic and hypotensive action, and action inhibiting the aggregation of platelets. The substances may be administered locally, orally or by injection using suitable pharmaceutical formulations in solid, liquid or suspension form (e.g. ointments, lotions, tablets, capsules, phials and syrups).

The following Examples illustrate the invention. The melting and boiling points are in degrees Centigrade and are uncorrected. The identity of the substances and their purity have been ascertained by elementary analysis of C, H, N (and halogens where present), infrared spectra, N.M.R. and U.V. analysis.

None of the products of this invention have yet been described in the literature.

The following Tables summarise certain pharmacological characteristics of some compounds of the present invention, the symbols of which have the following meanings:

LR 479 : 2-methyl-2-(β-N,N-diethylaminoethoxyethyl)-1,3-benzodioxole citrate
LR 498 : 2'-N,N-diethylaminoethoxymethyl-spiro(1,3-benzodioxale-2,1'-cyclohexane)citrate
LR 509 : 2-phenyl-2-(β-N,N-diethylaminoethoxyethyl)-1,3-benzodioxole citrate
LR 526 : 2-methyl-2-(β-piperidinoethoxyethyl)-1,3-benzodioxole citrate
LR 528 : 2-methyl-2-(γ-piperidinopropoxyethyl)-1,3-benzodioxole
LR 529 : 2-methyl-2-(β-N,N-diethylaminoethoxyethyl)-5-chloro-1,3-benzodioxole citrate
LR 530 : 2-methyl-2-(β-morpholinoethoxyethyl)-1,3-benzodioxole hydrochloride
LR 537 : 2,5-dimethyl-2-(β-N,N-diethylaminoethoxyethyl)-1,3-benzodioxole citrate
LR 538 : 2-methyl-2-(β-N,N-diethylaminoethoxyethyl)-4-methoxy-1,3-benzodioxole citrate
LR 543 : 2-methyl-2-(β-N,N-diethylaminoethoxyethyl)-1,3-naphthodioxole citrate
LR 554 : 2-methyl-2-(β-pyrrolidinoethoxyethyl)-1,3-benzodioxole
LR 564 : 2-methyl-2-(γ-N,N-dimethylaminopropoxyethyl)-1,3-benzodioxole hydrochloride
LR 604 : 2-methyl-2-(β-morpholinoethoxyethyl)-1,3-naphthodioxole citrate

TABLE I

| Substance | $DL_{50}$ mouse i.p. mg/Kg | $DL_{50}$ rat i.v. mg/Kg | Fibrillation by $CaCl_2$, anaesthetised rat | | Electrical stimulation, isolated atrium rabbit | | Arrhythmia by electrical stimulation, heart of anaesthetised cat | | | | Local anaesthesia mouse, $DE_{50}$ mg tot. i.d. |
|---|---|---|---|---|---|---|---|---|---|---|---|
| | | | $DE_{50}$ mg/Kg i.v. | Therapeutic index $DL_{50}/DE_{50}$ | $DE_{30}$ mcg/ml | Toxic dose | $DA_{100}$* mg/Kg i.v. | Arterial pressure change mm Hg | Lethal dose mg/Kg i.v. | Lethal dose $DA_{100}$ | |
| LR 479 | 75 | 15 | 2.50 | 6 | 2.0 | 100 | 1.50 | −22 | 7.5 | 5 | 0.5 |
| LR 498 | 75 | 8 | 0.37 | 21.6 | 3.40 | 10 | 2.8 | +20 | 14 | 5 | 1 |
| LR 509 | 35 | 5 | 1.50 | 3.33 | 1.0 | 10 | — | — | — | — | 0.5 |
| LR 526 | 75 | 8.50 | 1.75 | 4.86 | 2.10 | 100 | 5 | −30 | 10 | 2 | 1 |
| LR 528 | 75 | 8.50 | 1.75 | 4.86 | 2.60 | 100 | 2.2 | −17 | 14 | 6.36 | 1.5 |
| LR 529 | 150 | 18 | 3.75 | 4.8 | 1.42 | 100 | 3.3 | −65 | 15 | 4.55 | >2.0 |
| LR 530 | 300 | 50.0 | 6.25 | 8 | 17.0 | 100 | 5.8 | −20 | 45.0 | 7.76 | 2.0 |
| LR 537 | 100 | 12 | 1.20 | 10 | 4.50 | 100 | 2.8 | −45 | 13.5 | 4.82 | 2.0 |
| LR 538 | 75 | 9.8 | 1.50 | 6.53 | 10.50 | 100 | 1.8 | −30 | 17.0 | 9.45 | 1.5 |
| LR 543 | 150 | 24.0 | 3.50 | 6.86 | 17.50 | 30 | 2.8 | +10 | 25.0 | 8.93 | 2.0 |
| LR 554 | 80 | 23.0 | 3.75 | 6.14 | 1.35 | 100 | 2.1 | −25 | 14.0 | 6.67 | >2.0 |
| LR 564 | 100 | 17.5 | 5.25 | 3.34 | 5.01 | 100 | 3.7 | −20 | 18.0 | 4.87 | 2.0 |
| LR 604 | 150 | 35.0 | 5.0 | 7 | 3.0 | 100 | 2.8 | −20 | 25.0 | 8.93 | 1.0 |
| Procainamide | 312 | 90 | 15.0 | 6 | 42.0 | 1000 | 16 | −17 | 50.0 | 3.12 | 1.6 |

*dose which increases the threshold by 100%

TABLE II

| Substance | $DL_{50}$ mouse i.p. mg/Kg | Anti-aggregating activity, platelets in vitro $DE_{50}$ (mg/ml) | Increase in spontaneous motility $DE_{50}$ (mg/Kg os) mouse |
|---|---|---|---|
| LR 498 | 75 | 0.1 | 50 |
| LR 526 | 75 | 0.26 | — |
| LR 529 | 150 | 0.5 | — |
| LR 530 | 300 | 0.8 | — |
| LR 537 | 100 | 0.27 | — |
| LR 538 | 75 | 0.1 | — |
| LR 543 | 150 | 0.05 | 30 |
| LR 564 | 100 | 0.5 | — |

The anti-arrythmic activity was evaluated in the rat by the method of Malinow and coll. (Rev. Argent. Cardiol. 1952, 19, 120), in the isolated rabbit atrium by the Dawes method (Brit. J. Pharmacol. 1946, 1, 90), and in the cat heart, by electrical stimulation, by the Johnson method (Brit. J. Pharmacol. 1954, 9, 341).

The local anaesthetic activity was evaluated in the mouse by the Bianchi and Franceschini method (Brit. J. Pharmacol. 1954, 9, 280).

The changes in systemic arterial pressure in the cat (anaesthetised with chloralose-urethane) induced by drugs by intravenous administration were recorded by connecting an artery (generally the carotid) to a pressure transducer able to transmit a signal, suitably amplified, to a printout system.

The anti-aggregating activity on platelets was evaluated in the rabbit "in vitro" in accordance with the following method: the blood, withdrawn from conscious rabbits, was centrifuged in the presence of sodium citrate (3.8%) at 350 rpm for 10 minutes, to separate the plasma rich in platelets (PRP) from the rest. The aggregation of the platelets was carried out by bringing the PRP into contact with suitable doses of adenosine sodium diphosphate in the presence of a possible inhibitor or its carrier. The measurement of aggregation was made continuously by a turbidimetric method. The activity in stimulating the C.N.S. was evaluated in the mouse by the actophotometric method, which consists of placing the mice, 30 minutes after being treated orally with the drug or carrier, in a cage provided with a photoelectric cell and counting the number of times it passes in front of the photoelectric cell during a stay of 10 minutes.

EXAMPLE 1

2-methyl-2-(β-morpholinoethoxyethyl)-1,3-benzodioxole 3.2 g. of 80% NaH are added a little at a time, with cooling, to 10 g. of 2-methyl-2-(β-hydroxyethyl)-1,3-benzodioxole dissolved in 180 cc. of anhydrous benzene. The mixture is refluxed for one hour and cooled 15 g. of morpholino-ethyl chloride are added drop by drop, and the mixture is refluxed for three hours. The solvent is eliminated under vacuum, and the residue is dissolved in water, acidified with dilute HCl and extracted with ether. The aqueous phase is made alkaline and again extracted with ether. The organic phase is separated, dried over $Na_2SO_4$, and evaporated.

The hydrochloride is prepared from the residue (m.p 148°–9°).

In a like manner the following are prepared:

2-methyl-2-(β-piperidinoethoxyethyl)-1,3-benzodioxole (citrate m.p. 68°–9°)

2-methyl-2-(γ-piperidinopropoxyethyl)-1,3benzodioxole (b.p. 240°–60°/0.4 mm)

2-methyl-2-(β-N,N-diethylaminoethoxyethyl)-5-chloro-1,3-benzodioxole (citrate m.p. 93°–5°)

2,5-dimethyl-2-(β-N,N-diethylaminoethoxyethyl)-1,3-benzodioxole (citrate m.p. 93°–4°)

2-methyl-2-(β-morpholinoethoxyethyl)-1,3-naphthodioxole (citrate m.p. 109°–11°)

2-methyl-2-(β-N,N-diethylaminoethoxyethyl)-4-methoxy-1,3-benzodioxole (citrate m.p. 80°–1°)
2-methyl-2-(β-pyrrolidinoethoxyethyl)-1,3-benzodioxole (b.p. 170°–80°/0.3 mm)

EXAMPLE 2

2-methyl-2-(β-N,N-diethylaminoethoxyethyl)-1,3-benzodioxole 0.9 g. of 80% NaH are added a little at a time, with cooling, to 3.5 g. of N,N-diethylaminoethanol dissolved in 80 cc. of anhydrous benzene. The mixture is refluxed for 1 hour and cooled. 5.9 g. of 2-methyl-2-β-chloroethyl-1,3-benzodioxole are added drop by drop, and the mixture is refluxed for 3 hours. The solvent is eliminated under vacuum, and the residue is dissolved in water, acidified with dilute HCl, and extracted with ether. The aqueous phase is made alkaline, and again extracted with ether. The organic phase is separated, dried over Na$_2$SO$_4$, and evaporated. The citrate is prepared from the residue (m.p. 116°–7°).

In a like manner the following are prepared:
2-phenyl-2-(β-N,N-diethylaminoethoxyethyl)-1,3-benzodioxole (citrate, m.p. 100°–2°).
2'-N,N-diethylaminoethoxymethyl-spiro-(1,3-benzodioxole-2,1'-cyclohexane) (citrate, m.p. 111°–3°).
2-methyl-2-(γ-N,N-diethylaminopropoxyethyl)-1,3-benzodioxole (hydrochloride, 109°–11°).
β-N,N-diethylaminoethyl-thio-β-(2-methyl-1,3-benzodioxole-2-yl) ethane (citrate m.p. 136°–8°).
2-methyl-2-(β-N,N-diethylammoethoxyethyl)-1,3-naphthodioxole (citrate m.p. 135°–6°).

We claim:
1. A 1,3-benzodioxole of the formula

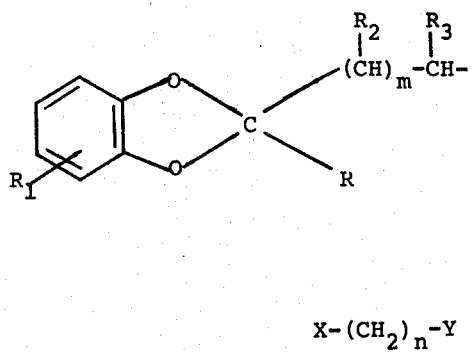

(I)

and its optical isomers, stereoisomers and pharmaceutically acceptable salts, in which R represents hydrogen, lower alkyl, halogeno(lower alkyl), hydroxy(lower alkyl), aryl, arylalkyl, or aryl or arylalkyl substituted in the aromatic ring by halogen, alkyl, hydroxyl or alkoxyl; R$_1$ represents hydrogen, one or more halogen atoms, lower alkyl, halogeno(lower alkyl), a

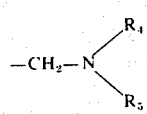

group wherein R$_4$ and R$_5$ are as defined below, hydroxyl, alkoxyl, a sulphonic acid group, sulphamido, N,N-dialkylsulphamido, nitro, amino, substituted amino, or alkylsulphonylamino, or R$_1$ is a benzene ring condensed on the benzodioxole nucleus; R$_2$ represents hydrogen, alkyl, aryl or hydroxyl; m represents 0, 1 or 2; R$_3$ represents hydrogen, lower alkyl, aryl, hydroxyl or cyano; n represents 0, 1, 2 or 3; X represents O or S; and Y represents hydrogen, aryl (substituted or unsubstituted in the aromatic ring by halogen, alkyl, hydroxyl or alkoxyl), a X—CH$_2$—CH$_2$—Y group, or a

group,
wherein R$_4$ and R$_5$ are hydrogen, lower alkyl, monocyclic carbocyclic aryl, or lower monocarbocyclic arylalkyl.

2. A 1,3-benzodioxole according to claim 1 and its pharmaceutically acceptable acid addition salts, in which R is alkyl of 1 to 4 carbon atoms or phenyl; R$_1$ is hydrogen, alkyl of 1 to 4 carbon atoms, chlorine, alkoxy of 1 to 4 carbon atoms, or the residue of a fused benzene ring; m is 0 or 1, R$_2$ and R$_3$ are each hydrogen or methyl; X is O or S; n is 2 or 3; and Y is dialkylamino of 1 to 4 carbon atoms in each alkyl.

3. A benzodioxole according to claim 1 which is 2-methyl-2-(β-N,N-diethylaminoethyl)-5-chloro-1,3-benzodioxole and its pharmaceutically acceptable salts.

4. A benzodioxole according to claim 1 which is 2,5-dimethyl-2-(β-N,N-diethylaminoethoxyethyl)-1,3-benzodioxole and its pharmaceutically acceptable salts.

5. A benzodioxole according to claim 1 which is 2-methyl-2-(β-N,N-diethylaminoethoxyethyl)-4-methoxy-1,3-benzodioxole and its pharmaceutically acceptable salts.

6. A benzodioxole according to claim 1 which is β-N,N-diethylaminoethyl-thio-β-(2-methyl-1,3-benzodioxol-2-yl)-ethane and its pharmaceutically acceptable salts.

7. A benzodioxole according to claim 1 which is 2-methyl-2-(β-N,N-diethylaminoethoxyethyl)-1,3-benzodioxole and its pharmaceutically acceptable salts.

8. A benzodioxole according to claim 1 which is 2-phenyl-2-(β-N,N-diethylaminoethoxyethyl)-1,3-benzodioxole and its pharmaceutically acceptable salts.

9. A benzodioxole according to claim 1 which is 2-methyl-2-(γ-N,N-dimethylaminopropoxyethyl)-1,3-benzodioxole and its pharmaceutically acceptable salts.

10. A benzodioxole according to claim 1 which is 2-methyl-2-(β-N,N-diethylaminoethoxyethyl)-1,3-naphthodioxole and its pharmaceutically acceptable salts.

11. A benzodioxole according to claim 1 in which R is alkyl of 1 to 4 carbon atoms, R$_1$ is hydrogen, alkyl of 1 to 4 carbon atoms, chlorine, an alkoxyl group of 1 to 4 carbon atoms, or the residue of a fused benzene ring, m is 1, R$_2$ and R$_3$ are each hydrogen, X is O or S, n is 2 and Y is dimethylamino or diethylamino.

12. A benzodioxole according to claim 11 in which R is methyl, R$_1$ is hydrogen, methyl, chlorine or methoxyl and X is O.

* * * * *